(12) United States Patent
Lim et al.

(10) Patent No.: US 8,109,976 B2
(45) Date of Patent: Feb. 7, 2012

(54) SYSTEMS AND METHODS FOR VERTEBRAL STABILIZATION

(75) Inventors: Roy K. Lim, Germantown, TN (US); William R. Sears, Sydney (AU)

(73) Assignee: Warsaw Orthopedic, Inc., Warsaw, IN (US)

( * ) Notice: Subject to any disclaimer, the term of this patent is extended or adjusted under 35 U.S.C. 154(b) by 294 days.

(21) Appl. No.: 12/469,865

(22) Filed: May 21, 2009

(65) Prior Publication Data

US 2010/0298881 A1 Nov. 25, 2010

(51) Int. Cl.
*A61B 17/70* (2006.01)

(52) U.S. Cl. .................. 606/278; 606/250; 606/251

(58) Field of Classification Search .......... 606/246–279
See application file for complete search history.

(56) References Cited

U.S. PATENT DOCUMENTS

| | | | |
|---|---|---|---|
| 5,112,332 A | 5/1992 | Cozad et al. | |
| 5,147,359 A | 9/1992 | Cozad et al. | |
| 5,154,718 A | 10/1992 | Cozad et al. | |
| 5,242,445 A * | 9/1993 | Ashman | 606/276 |
| 5,380,325 A * | 1/1995 | Lahille et al. | 606/250 |
| 5,669,911 A * | 9/1997 | Errico et al. | 606/264 |
| 5,716,355 A * | 2/1998 | Jackson et al. | 606/252 |
| 6,547,790 B2 | 4/2003 | Harkey, III et al. | |
| 6,832,999 B2 | 12/2004 | Ueyama et al. | |
| 7,666,210 B2 * | 2/2010 | Franck et al. | 606/250 |
| 2003/0045879 A1 | 3/2003 | Minfelde et al. | |
| 2003/0187438 A1 | 10/2003 | Assaker et al. | |
| 2005/0149021 A1 | 7/2005 | Tozzi | |
| 2006/0009766 A1 * | 1/2006 | Lee et al. | 606/61 |
| 2006/0058791 A1 | 3/2006 | Broman et al. | |
| 2006/0149231 A1 | 7/2006 | Bray et al. | |
| 2007/0055239 A1 * | 3/2007 | Sweeney et al. | 606/61 |
| 2007/0173829 A1 * | 7/2007 | Drewry et al. | 606/61 |
| 2008/0183217 A1 | 7/2008 | Glaser | |
| 2008/0228226 A1 | 9/2008 | Shamie | |
| 2008/0319483 A1 | 12/2008 | Triplett et al. | |
| 2008/0319484 A1 | 12/2008 | Fauth | |
| 2008/0319485 A1 | 12/2008 | Fauth et al. | |
| 2008/0319488 A1 | 12/2008 | Helgerson | |
| 2008/0319489 A1 | 12/2008 | Triplett | |
| 2009/0012566 A1 | 1/2009 | Fauth | |
| 2009/0062861 A1 | 3/2009 | Frasier et al. | |

OTHER PUBLICATIONS

International Searching Authority, International Search Report and Written Opinion, PCT App. No. PCT/US2010/035827, Date of mailing: Dec. 29, 2010.

* cited by examiner

*Primary Examiner* — Eduardo C Robert
*Assistant Examiner* — Christina Negrelli (57) ABSTRACT

Systems and methods for vertebral stabilization are provided. In one embodiment, a system includes a bone anchor with a threaded portion positioned opposite a post portion. A connector is provided including a pair of oppositely positioned branches defining a receptacle structured to receive the post portion. The receptacle is positionable between an open configuration and a closed configuration, wherein the connector is positionable along and about the post portion in the open configuration. The system also includes an elongate support member defining a passage structured to receive and engage a portion of the connector. As the connector is received in the passage, the branches of the connector move toward one another and force the receptacle toward the closed configuration wherein the connector is fixed relative to the post portion. Other systems, apparatuses and methods for vertebral stabilization are also disclosed.

14 Claims, 6 Drawing Sheets

SYSTEMS AND METHODS FOR VERTEBRAL STABILIZATION

BACKGROUND

The present invention relates to systems, apparatuses and methods for use in performing surgery in a patient, and more particularly, but not exclusively, relates to stabilization of vertebrae of a spinal column.

Various types of devices and systems have been used to stabilize portions of bones including the spine. Spinal stabilization techniques have utilized plating and rods on the posterior, anterior, lateral, postero-lateral and antero-lateral portions of a spinal column segment. Such systems can provide rigid or dynamic fixation of a spinal column segment for the repair of injured or diseased vertebrae, intervertebral discs, and other elements of the spinal column. Various anatomical considerations along the spinal column, such as bone degeneration and interference with neural elements and nerve tissues, can present difficulties in implementing stabilization systems and/or cause undesirable side effects once the stabilization systems have been implemented.

While developments in vertebral stabilization have provided steps in the right direction, there remains a need for further development in this area of technology.

SUMMARY

One non-limiting embodiment of the present application is directed to a system for providing stabilization between vertebrae of a spinal column.

In another embodiment, a system includes a first bone anchor with an elongated stem extending between a proximal end and a distal end. The elongated stem includes a threaded portion and a post portion. The system also includes a connector extending along a longitudinal axis between a first end and a second end and including a pair of oppositely positioned branches defining a receptacle structured to receive the post portion. The receptacle is generally positionable between an open configuration where the connector is free to move along and about the post portion, and a closed configuration where the connector is fixed relative to the post portion. An elongate support member including a shaft portion and a first end that includes a passage structured to receive and engage with a portion of the connector is also provided. As the portion of the connector is received by the passage of the first end of the elongate support member, the oppositely positioned branches of the connector move toward one another to force the receptacle toward the closed configuration to fix the connector relative to the post portion of the first bone anchor.

In a yet another embodiment, an apparatus includes a first bone anchor and a second bone anchor each including an elongated stem with a threaded portion and a post portion. The first and second bone anchors also each include a connector which includes a body with a receptacle structured to receive the post portion. The receptacle is positionable between an open configuration where the connector is movable along and around the post portion, and a closed configuration where the connector is fixed relative to the post portion. The apparatus also includes a first elongate support member and a second elongate support member each including an elongated shaft portion extending along a longitudinal axis between a first end and a second end. The first end of each of the first and second elongate support members includes a passage structured to receive and engage a portion of the connector of a respective one of the first and second bone anchors. A crosslink device structured to extend across a distance separating the first elongate support member and the second elongate support member when the first and second elongate support members engage with the connector of the respective one of the first bone anchor and the second bone anchor is also provided. The crosslink device includes a first member with a first end portion structured to engage with a first one of the first and second elongate support members, and a second member which includes a first portion and a second portion extending obliquely from the first portion. The second portion includes a second end portion structured to engage with a second one of the first and second elongate support members. The crosslink device also includes an interconnection device positioned between the first end portion and the second end portion to interconnect the first member and the second member.

In still another embodiment, a method for stabilizing vertebrae of a spinal column includes engaging a first bone anchor to a posterior arch of a first vertebra on a first side of a central axis of the spinal column, with the first bone anchor extending antero-laterally into a first lamina of the first vertebra from a first location adjacent to a midline of the posterior arch. The method also includes engaging a second bone anchor to the posterior arch of the first vertebra on a second side of the central axis of the spinal column, with the second bone anchor extending antero-laterally into a second lamina of the first vertebra from a second location adjacent to the midline of the posterior arch. The method further includes engaging a third bone anchor to a second vertebra, engaging a fourth bone anchor to the second vertebra, positioning a first elongate support member extending along a first longitudinal axis between the first bone anchor and the third bone anchor, and positioning a second elongate support member extending along a second longitudinal axis between the second bone anchor and the fourth bone anchor.

Another embodiment of the present invention is directed to a unique system for stabilization of vertebrae in a patient. Other embodiments include unique methods, systems, devices, kits, assemblies, equipment and/or apparatuses directed to vertebral stabilization. In still other embodiments, different forms and applications of the present invention are envisioned.

Further embodiments, forms, features, aspects, benefits, objects and advantages of the present invention shall become apparent from the detailed description and figures provided herewith.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices and described methods, and any such further applications of the principles of the invention as illustrated herein are contemplated as would normally occur to one skilled in the art to which the invention relates.

Figure 1:
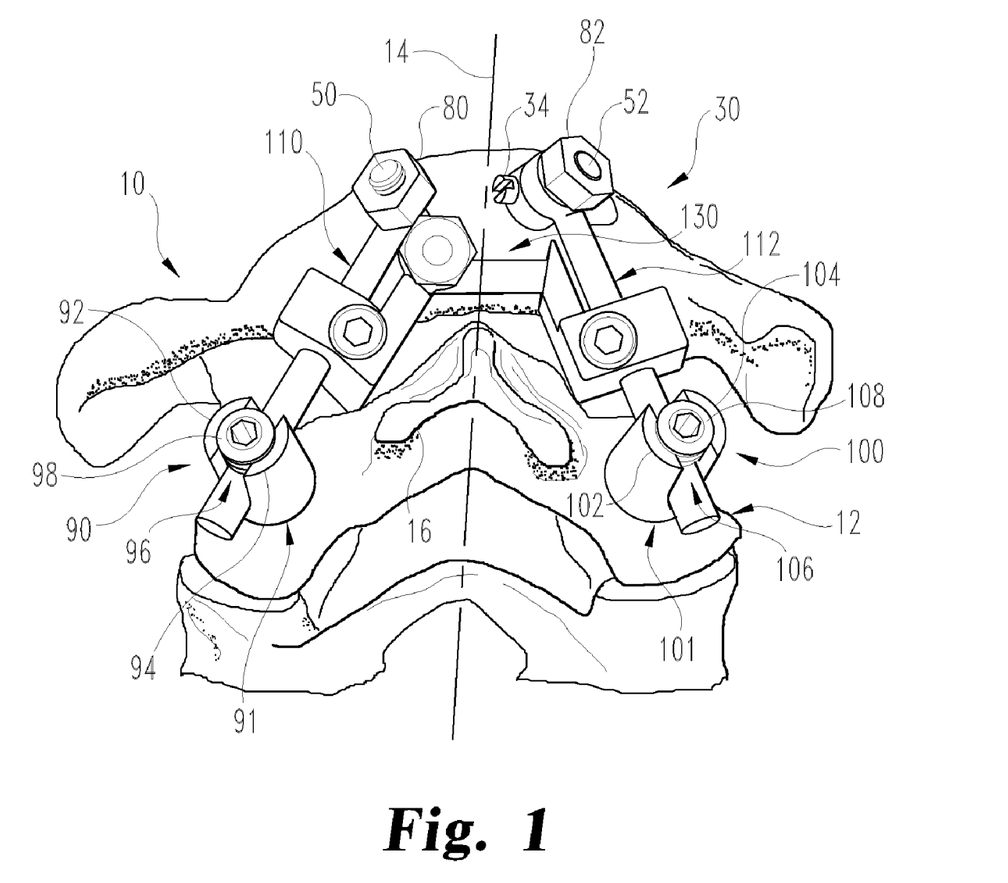
FIG. 1 is a posterior view of one embodiment of a vertebral stabilization system engaged with the spinal column of a patient.

Systems, apparatuses and methods for stabilizing vertebrae of the spinal column are provided. For example, with reference to FIG. 1, there is illustrated a spinal stabilization system 30 extending between a first vertebra 10 and a second, adjacent vertebra 12 and providing bilateral stabilization to the first and second vertebrae 10, 12. It is contemplated, however, that system 30 could extend between and provide stabilization between one or more vertebrae in addition to the first and second vertebrae 10, 12. Additionally, in the embodiment illustrated in FIG. 1, the first and second vertebrae 10, 12 represent the C1 and C2 cervical vertebrae, respectively, which are also commonly referred to as the atlas and axis vertebrae. However, it should be appreciated that the system 30 could be used to provide stabilization to other vertebrae in the cervical, thoracic and/or lumbar regions of the spine in addition to or in lieu of providing stabilization to the C1 and C2 cervical vertebrae. Moreover, while bilateral stabilization of the first and second vertebrae 10, 12 via the system 30 is illustrated in FIG. 1, it also contemplated that an alternative form of the system 30 could be utilized to provide uni-lateral stabilization of the first and second vertebrae 10, 12 on one side of central axis 14 along which the spinal column extends, further details of which will be set forth below.

The system 30 generally includes a first bone anchor 32 (shown in FIGS. 7-9) engaged to the first vertebra 10 on a first side of the central axis 14, a second bone anchor 34 engaged to the first vertebra 10 on an opposite second side of the central axis 14, a third bone anchor 90 engaged to the second vertebra 12 on the first side of the central axis 14, and a fourth bone anchor 100 engaged to the second vertebra 12 on the opposite second side of the central axis 14. The system 30 also includes a first elongate support member 110 extending between and coupled to the first bone anchor 32 and the third bone anchor 90, and a second elongate support member 112 extending between and coupled to the second bone anchor 34 and the fourth bone anchor 100. First and second connectors 50, 52 extend from the first and second bone anchors 32, 34, respectively, and are coupled to the first and second elongate support members 110, 112 via a respective first and second locking member 80, 82. The system 30 also includes a crosslink device 130 extending between and engaged with the first and second elongate support members 110, 112. Further details regarding these and other components of the system 30 will be described below in connection with FIGS. 1-5.

Figure 2:
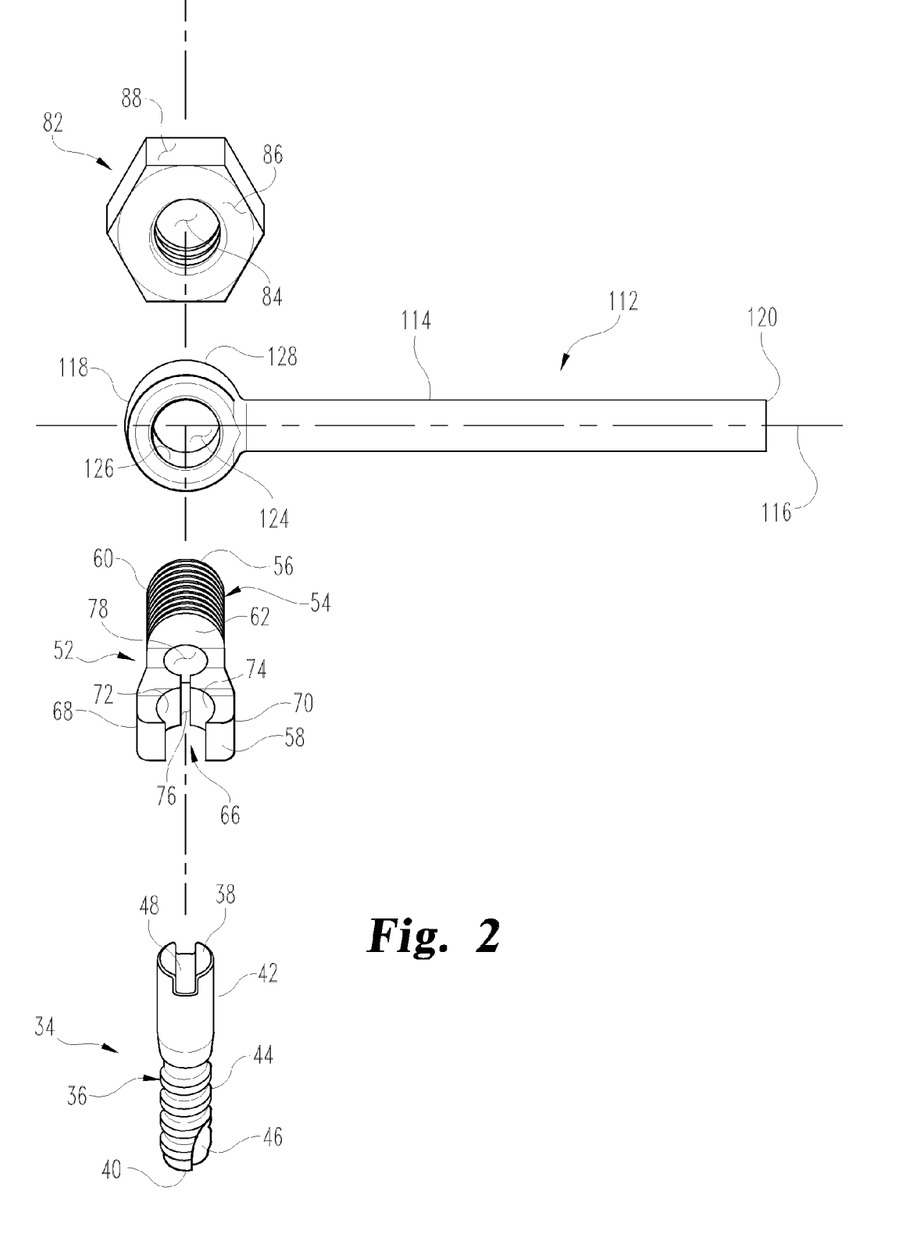
FIG. 2 is an exploded view of a bone anchor assembly and an elongate support member of the stabilization system illustrated in FIG. 1.

With reference to FIG. 2, there is illustrated an exploded assembly view of the structural features and the arrangement between the second bone anchor 34, the second connector 52, the second elongate support member 112, and the second locking member 82. While not illustrated in FIG. 2, it should be appreciated that the first bone anchor 32 is arranged with the first connector 50, the first elongate support member 110 and the first locking member 80 in a manner that is the same as or substantially similar to that described in connection with the arrangement illustrated in FIG. 2. Additionally, it should be appreciated that the first bone anchor 32, the first connector 50, the first locking member 80 and the first elongate support member 110 include features that are similar to or the same as the features described below in connection with the second bone anchor 34, the second connector 52, the second locking member 82 and the second elongate member 112, respectively.

The second bone anchor 34 includes an elongated shaft or stem 36 extending between a proximal end 38 and a distal end 40. The elongated stem 34 includes an external, helically threaded portion 44 structured to threadingly engage a passageway in one or more bones or bony structures, and can be provided with a cutting flute 46 or other structures that provide the threaded portion 44 with self-tapping and/or self-drilling capabilities. The elongated stem 36 can also be cannulated (not shown) to receive a guidewire to facilitate placement and may further include fenestrations or other openings for delivery of a bone growth material. The elongated stem 36 also includes a post portion 42 positioned generally opposite the threaded portion 44 and extending from the proximal end 38 toward the distal end 40. In the illustrated embodiment, the post portion 42 comprises an unthreaded and smooth shaft, and generally includes a continuous cylindrical cross-sectional configuration from the proximal end 38 to a proximal portion of the threaded portion 44, thereby resulting in the second bone anchor 34 having a headless configuration. However, in other non-illustrated forms, it is contemplated that the post portion 42 could include a tapered configuration between the proximal end 38 and the threaded portion 44 and/or a non-cylindrical cross-sectional configuration. Additionally, while the post portion 42 is illustrated as having a diameter that is slightly larger than the diameter of the threaded portion 44, it should be appreciated that in alternative forms, the post portion 42 could define a diameter that is the same or smaller than the diameter of the threaded portion 44. A tool engagement portion 48 is provided at the proximal end 38 of the second bone anchor 34 in the form of an elongated slot structured to receive a correspondingly shaped driving member. However, it should be appreciated that the tool engagement portion 48 may be provided as any of a number of suitable configurations in one or more alternative embodiments including, for example, an allen, phillips or square-drive configuration, or may be provided with an external driving configuration, such as a hex configuration.

Figure 3:
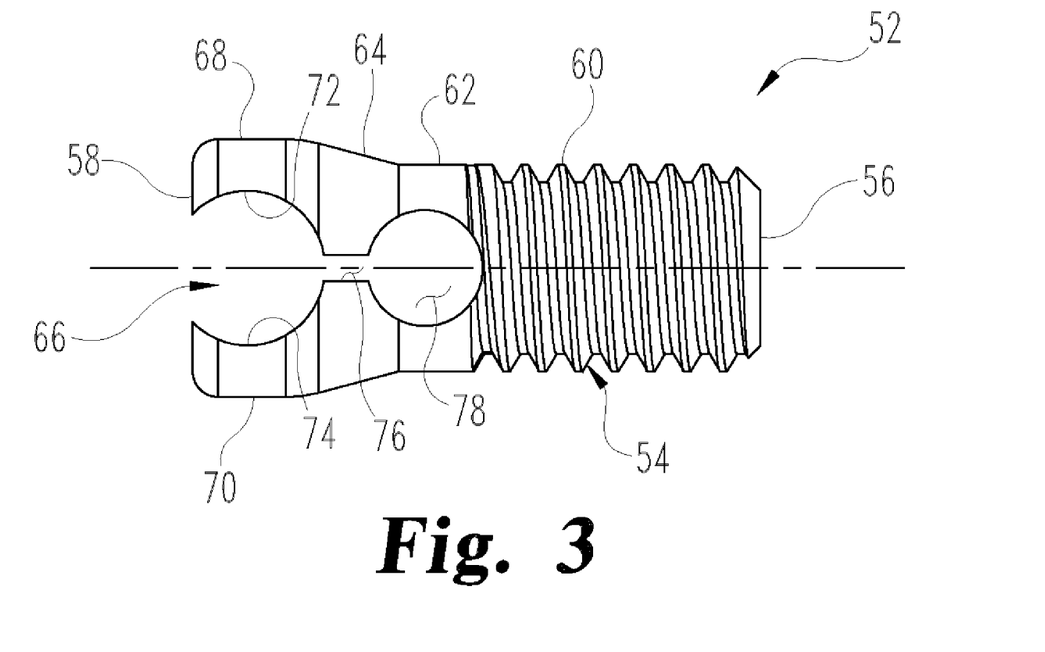
FIG. 3 is a side plan view of a connector illustrated in FIGS. 1 and 2.

As illustrated in FIGS. 2 and 3, the second connector 52 includes a body 54 extending between a first end 56 and an opposite second end 58. The body 54 includes an externally threaded portion 60 extending from the first end 56 toward the second end 58 to a smooth shaft portion 62. A tapered bearing surface 64 extends obliquely from the smooth shaft portion 62 toward the second end 58 to a first branch 68 and an opposite second branch 70. The body 54 also includes a receptacle 66 defined by opposing concavely curved inner surfaces 72, 74 of the first and second branches 68, 70, respectively. The receptacle 66 generally has a circular configuration sized and structured to generally correspond in size and shape with the post portion 42 of the second bone anchor 34. A longitudinal slot 76 extends through the body 54 from the receptacle 66 to an aperture 78 positioned on the smooth shaft portion 62 and extending partially into the threaded portion 60. The longitudinal slot 76 and the aperture 78 are generally structured to provide flexibility to the branches 68, 70 to allow the branches 68, 70 to move relative to one another such that the receptacle 66 (and the branches 68, 70) are flexibly transitionable between an open configuration and a closed configuration. In one or more non-illustrated forms, it is contemplated that the second connector 52 may be provided without the aperture 78, with the longitudinal slot 76 alone providing the flexibility to allow the first and second branches 68, 70 to move relative to one another between the open and closed configurations.

When the receptacle 66 is in the open configuration, the second connector 52 can be positioned on the post portion 42 of the second bone anchor 34 and moved therealong and/or rotated thereabout until a desired position and orientation between the second bone anchor 34 and the connector 52 is obtained. Once the desired position and orientation between the second bone anchor 34 and the second connector 52 has been obtained, the first and second branches 68, 70 are moved together to force the receptacle 66 toward the closed configuration in order to fix the position of the second connector 52 along and about the post portion 42, with the second connector 52 extending transversely therefrom. In one embodiment, transitioning of the receptacle 66 between the open and closed configurations is accomplished via the flexibly resilient nature of the branches 68, 70. As illustrated in FIGS. 2 and 3, the receptacle 66 is truncated by the second end 58 of the body 54 such that a portion of the post portion 42 of the bone anchor 34 extends beyond the second end 58 of the body 54 when the post portion 42 is positioned in the receptacle 66. In this configuration, the second connector 52 is engageable to the post portion 42 even if the second bone anchor 34 is positioned against or close to another object, such as, for example, bone or bony tissue.

As illustrated in FIG. 2, the second elongate support member 112 includes an elongated shaft 114 extending along a longitudinal axis 116 between a first end 118 and a second end 120. The elongated shaft 114 may be solid or hollow along some or all of its length and/or may be of a homogenous or heterogeneous composition. In addition, the elongated shaft 114 can be rigid or flexible and/or may include one or more flexible portions to permit at least limited spinal motion. While the elongated shaft 114 is illustrated as having a length sized to extend between the second bone anchor 34 and the fourth bone anchor 100, it should be appreciated that elongated shaft 114 could be provided with a length sized to extend to bone anchors attached to one or more vertebrae beyond the second vertebra 12. Additionally or alternatively, one or more connectors may be coupled to the elongated shaft 114 to facilitate interconnection of the second elongate supper member 112 to another elongate support member extending beyond the second vertebra 12.

The first end 118 of the elongate support member 112 is generally annular or hoop-shaped and defines a passage 124 extending therethrough sized and structured to receive and be positioned over the threaded portion 60 of the second connector 52. In the illustrated embodiment, the passage 124 is formed as a closed aperture. However, in alternative embodiments, passage 124 may be provided in a form other than a closed aperture. In one such variation, the passage 124 may be provided as an open collar defining a transverse slot. A chamfer or taper 126 may be provided along the ends of the passage 124 in order to assist in positioning of the threaded portion 60 of the second connector 52 in the passage 124 and/or to assist engaging the first end 118 with the bearing surface of 64 of the body 54 of the second connector 52.

The second locking member 82 includes an internally threaded aperture 84 structured to threadingly engage the threaded portion 60 of the second connector 52. The second locking member 82 includes a hexagonal external configuration having a plurality of drive faces 88 structured to facilitate engagement of the second locking member 82 with a similarly configured driving instrument. As the second locking member 82 is engaged with and threaded along the threaded portion 60 of the second connector 52, a bearing end surface 86 contacts an upper surface 128 of the first end 118 of the second elongate support member 112 and forces the first end 118 toward the second end 58 of the second connector 54. As the first end 118 is forced toward the second end 58 of the second connector 54, the passage 124 engages and bears against the tapered bearing surface 64, thereby forcing the first and second branches 68, 70 toward one another and compressing the receptacle 66 toward the closed configuration to clamp the branches 68, 70 around the post portion 42 of the second bone screw 34 in order to fix the relationship between the second bone anchor 34 and the second connector 52.

As indicated above, the first and second elongate support members 110, 112 are also connected to the third and fourth bone anchors 90, 100, respectively. In the illustrated embodiment, the third bone anchor 90 is provided with a receiving member 91 that includes a pair of laterally spaced branches 92, 94 extending generally parallel to one another. The branches 92, 94 form a U-shaped channel 96 therebetween that opens at the top of the receiving member 91 to allow the elongate support member 110 to be top-loaded into the U-shaped channel 96 between the branches 92, 94 for seating the elongate support member 110 against or adjacent to a bottom surface of the channel 96. The external surfaces of the branches 92, 94 can be curved or can be generally planar, and may be provided with surface features (not shown) that are structured to facilitate engagement with various instruments, such as driving instruments, reducers, and/or compression and distraction instruments that can be utilized to drive the third bone anchor 90 into bone and/or manipulating the third bone anchor 90 after it is engaged to bone.

The branches 92, 94 are provided with internal threading structured to threadingly engage an externally threaded set screw 98. The threaded set screw 98 can be provided with a recessed tool engagement portion and/or can include a frangible portion that breaks off when a threshold amount of torque is applied thereto during engagement with the receiving member 91. When engaged with the receiving member 91, the set screw 98 bears against the first elongate support member 110 to fix its positioning relative to the third bone anchor 90. In alternative embodiments not shown, receiving member 91 may include the channel 96, but not the internal threading, or may include external threading in addition to or in lieu of the internal threading. The U-shaped channel 96 can also form a channel structured to passively secure the first elongate support member 110 in the receiving member 91 without additional securing means. In one form, the bottom surface of the channel 96 can be concavely curved so as to form a portion of a circle to receive the elongated shaft portion of the first elongate support member 110 in form fitting or mating engagement. Other embodiments contemplate that the first elongate support member 110 may be positioned against a head of a bone screw, or against a cap or crown adjacent a head of a bone screw in the receiving member 91. In other non-illustrated embodiments, the receiving member 91 may be in the form of a post, saddle, clamp, top-loading connector, side-loading connector, bottom-loading connector, or any other suitable device for engaging the first elongate support member 110 with the third bone anchor 90.

Similar to the third bone anchor 90, the fourth bone anchor 100 has a receiving member 101 that includes a pair of laterally spaced branches 102, 104 extending generally parallel to one another. The branches 102, 104 form a U-shaped channel 106 therebetween that opens at the top of the receiving member 101 to allow the elongate support member 112 to be top-loaded into the channel 106 between the branches 102, 104 for seating against or adjacent to a bottom surface of the channel 106. The external surfaces of the branches 102, 104 can be curved or generally planar, and may be provided with surface features (not shown) that facilitate engagement of various instruments, such as driving instruments, reducers, and compression and distraction instruments, that can be utilized in driving the fourth bone anchor 100 into bone and/or manipulating the fourth bone anchor 100 after it is engaged to bone.

The branches 102, 104 can include an internal threading structured to threadingly engage an externally threaded set screw 108. The threaded set screw 108 can be provided with a recessed tool engagement portion and/or a frangible portion that breaks off when a threshold amount of torque has been applied thereto during engagement with the receiving member 101. When engaged with the receiving member 101, the set screw 108 bears against the second elongate support member 112 to fix its positioning relative to the fourth bone anchor 100. In alternative embodiments not shown, receiving member 101 includes the channel 106 but does not include internal threading, or may include external threading in addition to or in lieu of internal threading. The channel 106 can also form a channel structured to passively secure the second elongate support member 112 in the receiving member 101 without additional securing means. In one form, the bottom surface of the channel 106 can be concavely curved to form a portion of a circle to receive the elongated shaft portion 114 of the second elongate support member 112 in form fitting or mating engagement. Other embodiments contemplate that the second elongate support member 112 is positioned against a head of a bone screw, or against a cap or crown adjacent a head of a bone screw in the receiving member 101. In other non-illustrated embodiments, the receiving member 101 may be in the form of a post, saddle, clamp, top-loading connector, side-loading connector, bottom-loading connector, or any other suitable device for engaging the second elongate support member 112 with the fourth bone anchor 100.

While not specifically illustrated in FIG. 1, it should be appreciated that, in addition to the receiving members 91, 101, each of the third and fourth bone anchors 90, 100 also includes a bone engaging portion in the form of an externally threaded stem. However, alternative forms of the bone engaging portions are contemplated including, for example, hooks, staples, and interbody devices, just to provide a few possibilities. In addition, it is contemplated that the third and fourth bone anchors 90, 100 could each be provided with different forms of the bone engaging portions. The third and fourth bone anchors 90, 100 may include, but are not limited to, multi-axial, poly-axial, uni-axial and/or uni-planar configurations where the receiving members 91, 101 and the bone engaging portions are movable relative to one another. In one movable form, the receiving members 91, 101 and the bone engaging portions are engaged together via a "ball and joint" or swivel type of coupling element that permits relative movement therebetween during at least some stages of assembly and/or implantation.

Figure 4:
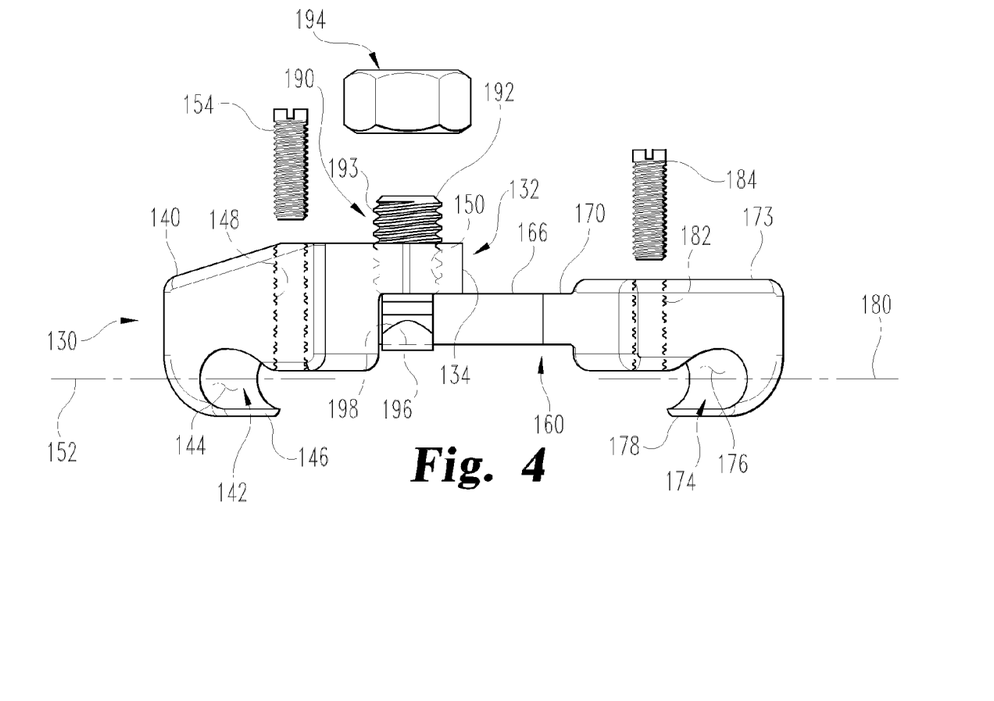
FIG. 4 is a partially exploded perspective view of a crosslink device of the stabilization system illustrated in FIG. 1.
Figure 5:
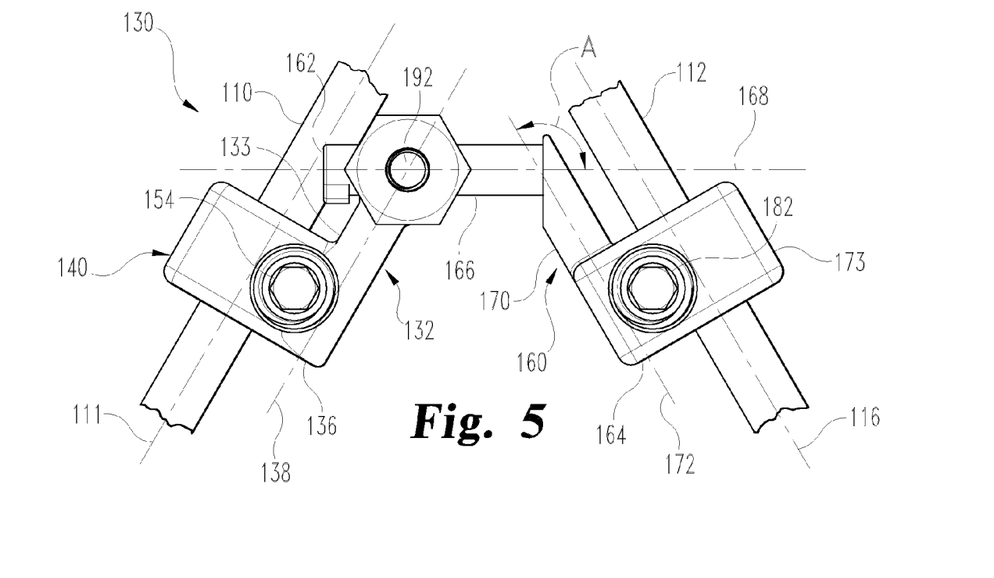
FIG. 5 is a top plan view of the crosslink device illustrated in FIG. 4, as positioned relative to other components of the system illustrated in FIG. 1.

With reference to FIGS. 4 and 5, further details regarding the crosslink device 130 are provided. More particularly, the crosslink device 130 includes a first bridging member 132, a second bridging member 160 and an adjustable linking/interconnection device 190 that interconnects the first and second bridging members 132, 160 and allows variation of the angular orientation and distance between the first and second bridging members 132, 160. The first and second bridging members 132, 160 extend between and interconnect the first and second elongate support members 110, 112. In the operational configuration illustrated in FIG. 1, the interconnection device 190 is superiorly offset toward the first vertebra 10 from the ends of the first and second bridging members 132, 160, and is also positioned to one side of the central axis 14. Moreover, the illustrated operational configuration of the crosslink device 130 allows positioning between the first and second elongate support members 110, 112 without interference with the spinous process 16 extending posteriorly from the second vertebra 12. It should be appreciated, however, that alternative configurations for the crosslink device 130 are also contemplated.

The first bridging member 132 includes an elongate portion 133 that extends along a longitudinal axis 138 between a first end 134 and a second end 136, with the first end 134 including a passage 150 extending therethrough. The second end 136 includes an elongated end portion 140 that extends in a transverse direction relative to the longitudinal axis 138 in a perpendicular or substantially perpendicular orientation. The end portion 140 includes a receiving portion 142 that includes a concavely curved inner surface 144 structured to receive and engage a portion of the first elongate support member 110. In the illustrated embodiment, the inner surface 144 extends to a lip 146 configured to provide support to at least a portion of the first elongate support member 110 when positioned in the receiving portion 142. The receiving portion 142 extends along a longitudinal axis 152 that is substantially parallel to the longitudinal axis 138 of the elongate portion 133 of the first member 132. In one or more non-illustrated forms, variations in the relative positioning between the elongate portion 133 and the receiving portion 142 are contemplated such that the axes 138, 152 could also be provided in a non-parallel configuration to define an angle of intersection between about 0 and about 30 degrees. Additionally, as illustrated in FIG. 4, the longitudinal axis 152 also substantially corresponds to and extends in line with the longitudinal axis 111 of the first elongate support member 110 when the member 110 is received by the receiving portion 142 and is positioned against and extends along the inner surface 144. However, it is also contemplated that the first elongate support member 110 could be positioned in the receiving portion 142 and only bear against a portion of the inner surface 144 such that the axes 111, 152 extend obliquely to one another in a non-parallel orientation.

Once the first elongate support member 110 is positioned within the receiving portion 142, a threaded fastener 154 is threadingly engaged within an internally threaded passage 148 extending through the end portion 140 and into communication with the receiving portion 142. A portion of the threaded fastener 152 extends through the passage 148 and into engagement with a portion of the first elongate support member 110 to force the first elongate support member 110 into abutting contact with at least a portion of the inner surface 144 in order to secure the first elongate support member 110 in the receiving portion 142.

The second bridging member 160 extends between a first end 162 and a second end 164 and includes a first portion 166 that extends along a longitudinal axis 168 and a second portion 170 that extends obliquely to the first portion 166 along a longitudinal axis 172. As illustrated in FIG. 4, the axes 168, 172 intersect one other at an angle A from about 110 degrees to about 130 degrees. However, in one or more alternative forms, it is contemplated that the first portion 166 and the second portion 170 could alternatively be configured relative to one another such that the axes 168, 172 intersect each other at an angle A from about 100 to about 140 degrees. Further variations in the angle A between the axes 168 and 172 are also contemplated.

The second end 164 of the second bridging member 160 includes an elongated end portion 173 that extends transversely to the longitudinal axis 172 in a perpendicular or substantially perpendicular orientation. The end portion 173 includes a receiving portion 174 that defines concavely a curved inner surface 176 structured to receive and engage a portion of the elongated shaft 114 of the second elongate support member 112. In the illustrated embodiment, the inner surface 176 extends to a lip 178 configured to provide support to at least a portion of the second elongate support member 112 when it is positioned in the receiving portion 174. The receiving portion 174 extends along a longitudinal axis 180 that is substantially parallel to the longitudinal axis 172 of the second portion 170 of the second member 160. In one or more non-illustrated forms, variations in the relative positioning between the second portion 170 and the receiving portion 174 are contemplated such that the axes 172, 180 could also be provided in a non-parallel configuration to define an angle of intersection between about 0 and about 30 degrees. In addition, as illustrated in FIG. 4, the longitudinal axis 180 also substantially corresponds to and extends in line with the longitudinal axis 116 of the second elongate support member 112 when it is received in the receiving portion 174 and is positioned against and along the inner surface 176. However, it is also contemplated that the second elongate support member 112 could be positioned in the receiving portion 174 so as to bear against a portion of the inner surface 176 such that the axes 116, 180 extend obliquely to one another in a non-parallel orientation.

Once the second elongate support member 112 has been positioned in the receiving portion 174, a threaded fastener 184 can be threadedly engaged within an internally threaded passage 182 extending through the end portion 173 and into communication with the receiving portion 174. A portion of the threaded fastener 184 extends through the passage 182 and into engagement with a portion of the second elongate support member 112 to force the second elongate support member 112 into abutting contact with at least a portion of the inner surface 176 in order to secure the second elongate support member 112 in the receiving portion 174.

As illustrated in FIG. 4, the adjustable linking/interconnection device 190 includes a stem 192, an internally threaded fastener 194, and a sleeve 196 defining a passageway 198. The sleeve 196 is positioned opposite the stem 192. The passage 150 in the first end 134 of the first bridging member 132 is structured to engage and be positioned about the stem 192 to allow rotation of the first bridging member 132 about the stem 192. Additionally, the passageway 198 is structured to receive the first end 162 of the second bridging member 160 to allow translational and rotatable movement of the second bridging member 160 relative to the passageway 198 and the interconnection device 190.

When the stem 192 is positioned through the passage 150 and the first end 162 of the second bridging member 160 extends through the passageway 198, the rotational positioning of the first bridging member 132 relative to the interconnection device 190 and the rotational and translational positioning of the second bridging member 160 relative to the interconnection device 190 may be determined. Once the relative positioning of the first and second bridging members 132, 160 has been determined, the fastener 194 is engaged with the external threading 193 on the stem 192. As the fastener 194 is turned, the sleeve 196 brings the first end 134 of the first bridging member 132 into abutting contact with the first portion 166 of the second bridging member 160, thereby forming a bearing relationship that resists movement therebetween. Correspondingly, the bridging members 132, 160 become fixed relative to one another as the fastener 194 is tightened on the stem 192 to bear against a side of the first end 134 of the first bridging member 132 opposite the side in contact with the second bridging member 160. It should be appreciated that before final tightening, refinements can be made to the relative positioning of the bridging member 132, 160. Once the fastener 194 is finally tightened, a bridging construct is provided that spans between the first and second elongate support members 110, 112.

Figure 6:
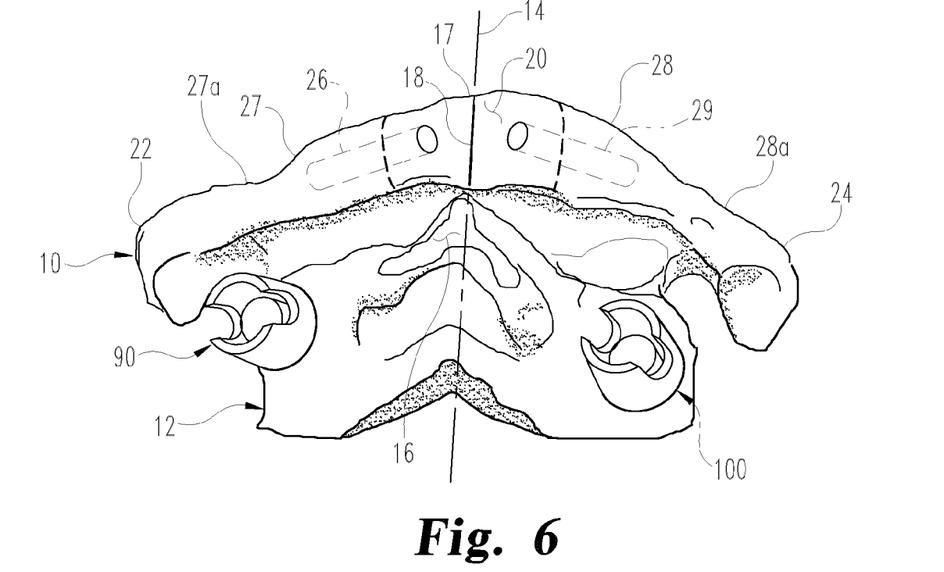
FIG. 6 is an enlarged posterior view of adjacent vertebrae illustrating various aspects of one procedure for installing the stabilization system of FIG. 1.

With reference to FIGS. 6-9, further aspects of one non-limiting procedure for positioning and engaging the system 30 between the first and second vertebrae 10, 12 will be described, although it should be appreciated that alternative procedures for positioning the system 30 are also contemplated. In FIG. 6, each of the third and fourth bone anchors 90, 100 have been engaged with the lower vertebra 12. It should be appreciated that the third and fourth bone anchors 90, 100 can be engaged with the second vertebra 12 in any suitable manner and at any suitable location including, for example, the inferior articular process or the pars interarticularis, just to provide a few non-limiting possibilities. In one non-illustrated form, openings that are sized and configured for receiving the bone engaging portions of the third and fourth bone anchors 90, 100 are formed in the second vertebra by removing or cutting material, reaming, drilling, and/or tapping.

The first and second bone anchors 32, 34 are engaged with the posterior arch 17 of the first vertebra 10. More particularly, as illustrated in FIG. 6, a first passageway 26 and a second passageway 29 are formed in the posterior arch 17 and are structured to receive the first and second bone anchors 32, 34, respectively. The first and second passageways 26, 29 may be formed by removing or cutting material, reaming and/or drilling, and may also be tapped to form internal threadings along the passageways 26, 29. In the illustrated form, the first and second passageways 26, 29 begin at locations laterally adjacent the midline 18 of the posterior arch 17 and extend antero-laterally from these locations in an oblique orientation relative to the central axis 14 toward the lateral masses 22, 24, respectively, of the first vertebra 10. The passageways 26, 29 are formed within and enclosed by the bone and bony tissue of a first lamina 27 and a second lamina 28 of the first vertebra 10. Similarly, when the first and second bone anchors 32, 34 are engaged with the passageways 26, 29, each is positioned within and surround by the bone and/or bony tissue of the laminae 27, 28. Additionally, in FIG. 6, the depth of the passageways 26, 29 is such that each terminates before entering the reduced mass portions 27a, 28a of the respective laminae 27, 28 adjacent the lateral masses 22, 24, although alternative depth arrangements for the passageways 26, 29 are also contemplated.

Figure 7:
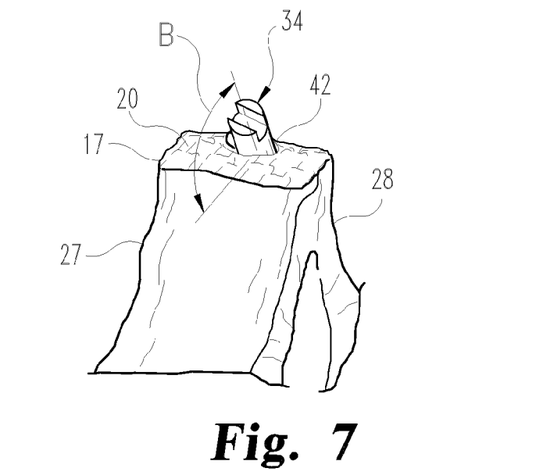
FIG. 7 is a lateral view of one of the vertebrae illustrated in FIG. 6.

In the illustrated embodiment, at least some bone and/or bony tissue has been removed from the posterior arch 17 to provide an area 20 of reduced thickness extending across the midline 18. The area 20 generally includes a planar surface that extends substantially normal to the central axis 14 in the coronal plane, as illustrated in FIG. 7, and its reduced thickness may generally assist in aligning and placing the passageways 26, 29 within the laminae 27, 28. Moreover, as also illustrated in FIG. 7 where the second bone anchor 34 has been engaged with the second passageway 29, the orientation of the second passageway 29 positions the anterior side of the post portion 42 of the second bone anchor 34 in close proximity to the bone of the posterior arch 17 adjacent the area 20. Additionally, when engaged in the second passageway 29, the second bone anchor 34 forms an angle B with the planar surface of the area 20 from about 2 degrees to about 40 degrees, although other angles are also contemplated. For example, in one alternative form, the angle B could range from about 5 degrees to about 20 degrees. Additionally, while not illustrated with respect to the first bone anchor 32, it should be appreciated that the first bone anchor 32 can extend relative to the area 20 in an angular orientation similar to that described above with regard to the second bone anchor 34. It should also be appreciated that procedures are contemplated where the passageways 26, 29 are formed in the laminae 27, 28 and the first and second bone anchors 32, 34 are engaged therein without forming the area 20 extending across the midline 18.

Figure 8:
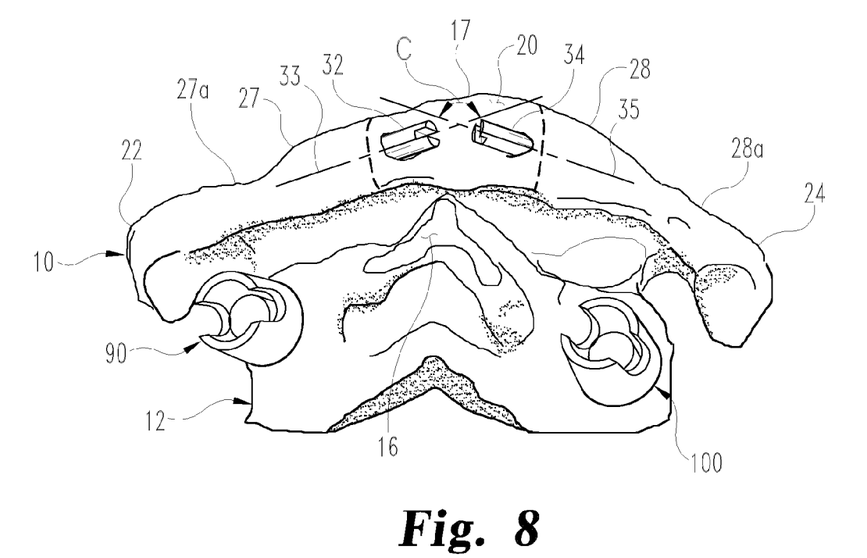
FIG. 8 is an enlarged posterior view of the adjacent vertebrae of FIG. 6 illustrating various aspects of one procedure for installing the stabilization system of FIG. 1.

In FIG. 8, the first and second bone anchors 32, 34 are engaged with the passageways 26, 29, respectively. As illustrated, the longitudinal axis 33 of the first bone anchor 32 and the longitudinal axis 35 of the second bone anchor 34 intersect one another at a location posterior to the posterior arch 17 at an angle C, which in one form may fall within a range from about 100 degrees to about 150 degrees. In another form, the angle C may fall within a range from about 110 degrees to about 140 degrees, although further variations of angle C are also contemplated. With the first and second bone anchors 32, 34 engaged with the first vertebra 10, the first and second connectors 50, 52 are engaged with the non-threaded post portions 42 of the anchors, with the connectors 50, 52 in turn coupled to the first and second elongate support members 110, 112.

Figure 9:
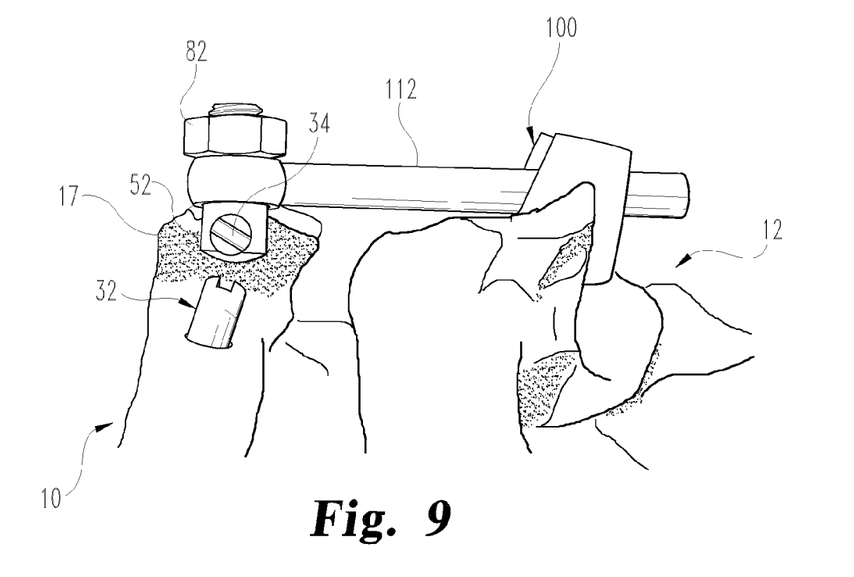
FIG. 9 is a lateral view of one of the vertebrae illustrated in FIG. 6 illustrating various aspects of one procedure for installing the stabilization system of FIG. 1.

For example, as illustrated in FIG. 9, the second connector 52 has been positioned on the second bone anchor 34, with the second end 58 thereof positioned adjacent to the posterior arch 17. The first end 118 of the second elongate support member 112 is positioned about the second connector 52, and the elongated shaft 114 is positioned in the channel 106 of the fourth bone anchor 100. The second locking member 82 and the set screw 108 may be provisionally tightened with the second connector 52 and the fourth bone anchor 100, respectively. In one form, the second connector 52 and the first end 118 of the second elongate support member 112 may be provisionally coupled together with the locking member 82 before the second connector 52 is laterally slid into position on the post portion 42 of the second bone anchor 42. However, alternative variations for the assembly of the system 30 are also contemplated. Additionally, it should be appreciated that the first elongate support member 110 can be positioned between and connected to the first bone anchor 32 and the third bone anchor 90 in a manner similar to that described above with respect to the second elongate support member 112.

The first and second elongate support members 110, 112 can be provisionally coupled or locked relative to the bone anchors 32, 34, 90, 100 with the locking members 80, 82 and the set screws 98, 108 until the crosslink device 130 is positioned between the elongate support members 110, 112 and a desired configuration of the system 30 is obtained. Once the desired configuration of the system 30 has been obtained, the locking members 80, 82, the set screws 98, 108 and the fastener 194 can be finally tightened to provide a rigid construct between the components of the system 30. As indicated above, in one non-illustrated form, the system 30 can be modified to provide uni-lateral stabilization. In this form, only one of the first and second bone anchors 32, 34 is engaged to the first vertebra 10 in the manner set forth above. A corresponding one of the third and fourth bone anchors 90, 100 is engaged to the second vertebra 12 and one of the elongate support members 110, 112 is positioned therebetween.

The components of the system 30 can be formed of medical grade stainless steel. Other embodiments include but are not limited to titanium, a titanium alloy or other metallic alloys and/or nonmetallic compositions.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as falling within the scope of the invention, that scope being defined by the claims that follow. In reading the claims, it is intended that when words such as "a," "an," "at least one," "at least a portion" are used, there is no intention to limit the claim to only one item unless specifically stated to the contrary. Further, when the language "at least a portion" and/or "a portion" is used, the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A system, comprising:
   a first bone anchor including an elongated stem extending between a proximal end and a distal end, said elongated stem including a threaded portion and a post portion;
   a monolithic connector extending along a longitudinal axis between a first end and a second end, said connector including a smooth shaft portion positioned between said first and second ends, said connector including a pair of oppositely positioned branches extending from said smooth shaft portion toward said second end and defining a receptacle structured to receive said post portion and positionable and transitionable between an open configuration and a closed configuration, said connector including a tapered portion extending obliquely from the smooth shaft portion toward each of said pair of branches, said tapered portions defining a first section approximate to said smooth shaft portion and having a first width and a second section approximate to said branches and having a second width, said second width greater than said first width;
   an elongate support member including a first end portion and a shaft portion, said first end portion defining a passage structured to receive and engage a portion of said connector, said passage having a third width greater than said first width and less than said second width; and
   wherein said oppositely positioned branches of said connector move toward one another to force said receptacle toward said closed configuration to fix said connector relative to said post portion of said first bone anchor as said portion of said connector is received by said passage defined by said first end portion of said elongate support member and said passage is translated from said first section toward said second section.

2. The system of claim 1, further comprising a second bone anchor including a bone engaging portion and a receiving member, said receiving member being multi-axially adjustable relative to said bone engaging portion and including a pair of laterally spaced branches defining a channel for receiving said shaft portion of said elongate support member.

3. The system of claim 1, wherein said post portion of said first bone anchor includes a continuous cross-sectional configuration from said proximal end to said threaded portion.

4. The system of claim 3, wherein said post portion of said first bone anchor is substantially cylindrical and each one of said pair of branches of said connector includes an arcuate inner surface, said arcuate inner surfaces defining said receptacle.

5. The system of claim 1, wherein said connector includes an externally threaded portion extending from said first end to said smooth shaft portion.

6. The system of claim 5, further comprising an internally threaded locking member structured to engage with said externally threaded portion of said connector and bear against said first end of said elongate support member when said portion of said connector is received by said passage.

7. An apparatus, comprising:
a first bone anchor and a second bone anchor each including an elongated stem with a threaded portion and a post portion, and a monolithic connector including a body having a pair of branches defining a receptacle and structured to receive said post portion, said receptacle being positionable between an open configuration wherein said connector is movable along and around said post portion and a closed configuration wherein said connector is fixed relative to said post portion, said connector including a smooth shaft portion positioned between a first end and said branches of said connector and a tapered portion extending obliquely from the smooth shaft portion toward each of said pair of branches, said tapered portions defining a first section approximate to said smooth shaft portion and having a first width and a second section approximate to said branches and having a second width, said second width greater than said first width;
a first elongate support member and a second elongate support member each including an elongated shaft portion extending along a longitudinal axis between a first end portion and a second end portion, said first end portion defining a passage structured to receive and engage with a portion of said connector of a respective one of said first bone anchor and said second bone anchor, said passage having a third width greater than said first width and less than said second width, wherein said branches move toward one another to force said receptacle toward said closed configuration as said portion of said connector is received by said passage and said passage is translated from said first section toward said second section; and
a crosslink device structured to extend across a distance separating said first elongate support member and said second elongate support member when said first and second elongate support members engage with said portion of said connector of said respective one of said first bone anchor and said second bone anchor, said crosslink device including:

a first member with a first end structured to engage with a first one of said first and second elongate support members;
a second member which includes a first portion and a second portion extending obliquely from said first portion, said second portion including a second end structured to engage with a second one of said first and second elongate support members; and
an interconnection device positioned between said first end and said second end to interconnect said first member and said second member together.

8. The apparatus of claim 7, wherein said first member of said crosslink device includes a shaft portion extending along a first axis and said first end includes a first receiving portion structured to receive said first one of said first and second elongate support members, said first receiving portion extending along a second axis that extends substantially parallel to said first axis and corresponds to the longitudinal axis of said first one of said first and second elongate support members when said first one of said first and second elongate support members is received by said first receiving portion.

9. The apparatus of claim 8, wherein said first portion of said second member extends along a third axis, said second portion of said second member extends along a fourth axis obliquely intersecting said third axis and said second end portion includes a second receiving portion structured to receive said second one of said first and second elongate support members, said second receiving portion extending along a fifth axis that extends substantially parallel to said fourth axis and corresponds to the longitudinal axis of said second one of said first and second elongate support members when said second one of said first and second elongate support members is received by said second receiving portion.

10. The apparatus of claim 9, wherein said third axis intersects said fourth axis at an angle from about 110 to about 130 degrees.

11. The apparatus of claim 7, wherein said receptacle of said connector is defined by a pair of oppositely positioned concavely curved surfaces and said body of said connector includes an externally threaded portion structured to engage with an internally threaded locking member, said engagability between said locking member and said connector providing a bearing force to position said receptacle toward said closed configuration.

12. The apparatus of claim 7, further comprising a third bone anchor and a fourth bone anchor each including a bone engaging portion and a receiving member, said receiving member being multi-axially adjustable relative to said bone engaging portion and including a pair of laterally spaced branches defining a channel for receiving a portion of a respective one of said first and second elongate support members.

13. The apparatus of claim 7, wherein said interconnection device further includes:
a connector body defining a stem to engage said first member with an adjustable range of first rotational positions relative to said stem and a passageway to receive said second member with an adjustable range of translational and second rotational positions relative to said passageway; and
a fastener structured to fix said first member relative to said stem at one of said first rotational positions when engaged to said stem and to fix said second member in said passageway at one of said translational positions and one of said second rotational positions.

14. An apparatus, comprising:
a first bone anchor and a second bone anchor each including an elongated stem with a threaded portion and a post portion, and a connector including a body with a receptacle structured to receive said post portion, said receptacle being positionable between an open configuration wherein said connector is movable along and around said post portion and a closed configuration wherein said connector is fixed relative to said post portion;
a first elongate support member and a second elongate support member each including an elongated shaft portion extending along a longitudinal axis between a first end portion and a second end portion, said first end portion defining a passage structured to receive and engage with a portion of said connector of a respective one of said first bone anchor and said second bone anchor, and
a crosslink device structured to extend across a distance separating said first elongate support member and said second elongate support member when said first and second elongate support members engage with said portion of said connector of said respective one of said first bone anchor and said second bone anchor, said crosslink device including:
a first member with a first end structured to engage with a first one of said first and second elongate support members;
a second member which includes a first portion and a second portion extending obliquely from said first portion, said second portion including a second end structured to engage with a second one of said first and second elongate support members; and
an interconnection device positioned between said first end and said second end to interconnect said first member and said second member together,
wherein said first member of said crosslink device includes a shaft portion extending along a first axis and said first end includes a first receiving portion structured to receive said first one of said first and second elongate support members, said first receiving portion extending along a second axis that extends substantially parallel to said first axis and corresponds to the longitudinal axis of said first one of said first and second elongate support members when said first one of said first and second elongate support members is received by said first receiving portion, and
wherein said first portion of said second member extends along a third axis, said second portion of said second member extends along a fourth axis obliquely intersecting said third axis and said second end portion includes a second receiving portion structured to receive said second one of said first and second elongate support members, said second receiving portion extending along a fifth axis that extends substantially parallel to said fourth axis and corresponds to the longitudinal axis of said second one of said first and second elongate support members when said second one of said first and second elongate support members is received by said second receiving portion.

* * * * *